United States Patent [19]

Greenlee et al.

[11] 4,402,969

[45] Sep. 6, 1983

[54] ANTIHYPERTENSIVE PROLINE DERIVATIVES

[75] Inventors: William J. Greenlee, Teaneck; David G. Hangauer, Jr., Fanwood; Arthur A. Patchett, Westfield, all of N.J.

[73] Assignee: Merck & Co., Inc., Rahway, N.J.

[21] Appl. No.: 340,241

[22] Filed: Jan. 21, 1982

Related U.S. Application Data

[63] Continuation-in-part of Ser. No. 246,491, Mar. 23, 1981, abandoned.

[51] Int. Cl.$^3$ .................... A61K 31/40; C07D 207/16
[52] U.S. Cl. .................................... 424/274; 424/258; 424/270; 548/201; 548/496; 548/533; 548/535; 546/147; 546/169
[58] Field of Search ..................... 424/274; 260/326.4; 548/533

[56] References Cited

U.S. PATENT DOCUMENTS

| 4,022,794 | 5/1977 | Smith et al. ........................ 424/263 |
| 4,052,511 | 10/1977 | Cushman et al. .................. 424/274 |
| 4,129,571 | 12/1978 | Ondetti et al. .................... 260/326.2 |
| 4,154,960 | 5/1979 | Ondetti et al. ...................... 562/462 |
| 4,294,832 | 10/1981 | Yoneda et al. ...................... 546/147 |

FOREIGN PATENT DOCUMENTS

| 18549 | 12/1980 | European Pat. Off. ............ 546/147 |
| 55/151555 | 11/1980 | Japan . |

OTHER PUBLICATIONS

Derwent Abstract of German Patent Application No. 2704-985.
Derwent Abstract of German Patent Application No. 2720-996.
Derwent Abstract of German Patent Application No. 2810-261.
Abst. of ACS Meeting of 9/11/78 "Superactive Analogs of the Angiotension Converting Enzyme Inhibitor BPP9a Containing L-3.4-Dehydroproline".

*Primary Examiner*—Jane T. Fan
*Attorney, Agent, or Firm*—Salvatore C. Mitri; Rudolph J. Anderson

[57] ABSTRACT

The invention relates to urea compounds which are useful as antihypertensives.

27 Claims, No Drawings

4,402,969

ANTIHYPERTENSIVE PROLINE DERIVATIVES

BACKGROUND OF INVENTION

This application is a continuation-in-part of application Ser. No. 246,491 filed Mar. 23, 1981 now abandoned.

The invention, in its broad aspects, relates to urea compounds which are useful in the treatment of hypertension. More specificially, this invention relates to urea analogs of dipeptides which, when derivatized as described herein, are potent converting enzyme inhibitors and useful antihypertensives. The compounds of this invention are represented by the following formula:

$$\begin{array}{c} R_1 \quad\quad R_2 \quad R_3 \\ | \quad\quad\quad | \quad\quad | \\ CH-CH_2-N-CON-CH-R_4 \\ | \quad\quad\quad\quad\quad\quad | \\ CO_2R \quad\quad\quad\quad CO_2R \end{array} \quad (I)$$

wherein
  R is the same or different and is hydrogen, loweralkyl, aralkyl;
  $R_1$ is alkyl of from one to ten carbon atoms which include branched, cyclic, and unsaturated alkyl groups; substituted alkyl of from one to six carbon atoms and the substituent is amino, arylthio, aryloxy, hydroxy, arylamino, and acylamino; aralkyl and heteroaralkyl optionally substituted by halo, loweralkyl, hydroxy, alkoxy, and amino groups wherein the alkyl groups contain from one to six carbon atoms;
  $R_2$ is hydrogen, alkyl of from one to six carbon atoms optionally substituted by amino, alkylamino, arylamino, acylamino, heteroaryl, or aryl groups;
  $R_3$ is hydrogen, loweralkyl;
  $R_4$ is alkyl of from one to six carbon atoms optionally substituted by aryl, heteroaryl, or amino groups; or,
  $R_3$ and $R_4$ may be connected together to form an alkylene bridge of from two to five carbon atoms; or, an alkylene bridge containing one sulfur atom and two to three carbon atoms optionally substituted by alkyl or aryl, or hydroxy substituted aryl groups; or, an alkylene bridge of from three to four carbon atoms containing a double bond; or, an alkylene bridge of three to four carbon atoms substituted by hydroxy or lower alkoxy; or, an alkylene bridge of from three to four carbon atoms bearing a benzofusion thereto such as, for example, 1,2,3,4-tetrahydro-3-isoquinolinecarboxylic acid; and,
the pharmaceutically acceptable salts thereof.

Preferred are those compounds of Formula I wherein:
  R is the same or different and is hydrogen, loweralkyl, aralkyl;
  $R_1$ is alkyl of from one to six carbon atoms optionally substituted by amino, hydroxyl, acylamino, aryloxy; aralkyl, and heteroaralkyl optionally substituted by halo, loweralkyl, hydroxy, alkoxy, and amino groups wherein the alkyl groups contain from one to six carbon atoms;
  $R_2$ is hydrogen or alkyl of from one to six carbon atoms optionally substituted by amino, or heteroaryl groups;
  $R_3$ is hydrogen;
  $R_4$ is alkyl of from one to six carbon atoms optionally substituted by aryl, heteroaryl or amino groups; or,
  $R_3$ and $R_4$ may be connected together to form an alkylene bridge of from three to four carbon atoms; or, an alkylene bridge containing one sulfur atom and two to three carbon atoms optionally substituted by a hydroxyphenyl group; or, an alkylene bridge of from three to four carbon atoms substituted by hydroxy or lower alkoxy; or, an alkylene bridge of from three to four carbon atoms bearing a benzofusion thereto. Still more preferred ring structures when
  $R_3$ and $R_4$ are joined through the carbon and nitrogen atoms are five and six membered rings having the formulae:

$$\begin{array}{cc} \text{Ar} & \\ \diagdown & \\ \rangle\!-\!X & m(CH_2)\!-\!\!\!\diagup\!\!\!\diagdown \\ N\; | & \text{and} \quad N\;\diagup \quad | \\ \diagup & \diagdown\!-\!(CH_2)_n \\ \rangle\!-\!(CH_2)_l & CO_2H \\ CO_2H & \end{array}$$

wherein X is $CH_2$, S, CHOH, $CHOCH_3$; l is one; m is 0 or one; n is one or two; and Ar is phenyl, 2-hydroxyphenyl, or naphthyl.

Most preferred are compounds of Formula I wherein
  R is the same or different and is hydrogen or loweralkyl;
  $R_1$ is aralkyl and heteroaralkyl, wherein the alkyl groups contain one to three carbon atoms;
  $R_2$ is hydrogen, alkyl of from one to six carbon atoms, or amino substituted alkyl of from one to six carbon atoms; and,
  $R_3$ and $R_4$ are joined through the carbon and nitrogen atoms to which they are attached to form ring structures which are members of the group consisting of proline, 4-thiaproline, 2-(2-hydroxyphenyl)-thiazolidene-4-carboxylic acid, 1,2,3,4-tetrahydro-3-isoquinolinecarboxylic acid, and 1,2,3,4-tetrahydroquinoline-2-carboxylic acid.

The preferred, more preferred and most preferred compounds also include the pharmaceutically acceptable salts thereof.

The loweralkyl groups, except where noted otherwise, are straight and branched chain hydrocarbon radicals of from one to six carbon atoms such as, for example, methyl, ethyl, isopentyl, and the like. The aralkyl groups, unless noted otherwise, refer to lower alkyl groups substituted by phenyl or naphthyl. Acyl, where it appears, is lower alkanoyl or aroyl. Halo means chloro, bromo, iodo or fluoro. Aryl where it appears represents phenyl, naphthyl or biphenyl. Heteroaryl groups, where they appear, include for example, pyridyl, thienyl, furyl, imidazolyl, indolyl, benzthienyl or thiazolyl. Aryloxy, arylthio and arylamino refer to groups in which substituent linkages are made to the heteroatoms; i.e., oxygen, nitrogen and sulfur, and, wherein aryl is as defined above. Examples of such groups include β-naphthyloxy, thiophenoxy 4-biphenylamino, and the like.

The compounds of this invention are synthesized by the methods described below. Unless otherwise indicated, starting materials required for the below-described processes are known in the literature or can be made by known methods using known starting materials. Reactive, interfering functionality in these starting materials such as, for example, hydroxy, phenolic, carboxylic acid or amino groups, can be masked by protecting groups which can then be subsequently removed to afford the end products desired. Appropriate protecting groups are illustrated in the processes described herein and are well known to those skilled in the art of peptide chemistry. In the description of the processes which follow, R, $R_1$, $R_2$, $R_3$, $R_4$, and X are as defined above unless otherwise indicated.

REACTION SCHEME I

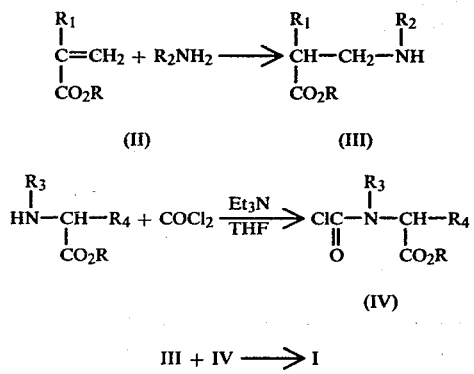

III + IV ⟶ I

REACTION SCHEME II

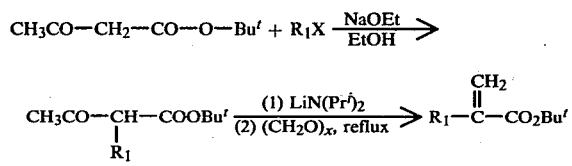

In Reaction Scheme I, the Michael addition of $R_2NH_2$ to the substituted acrylic acid or ester (II) is generally conducted at room temperature in an inert solvent.

Many acrylic esters and acids are known in the literature. New acrylic esters and acids can be synthesized by processes analogous to those reported in the literature such as that shown, for example, in Reaction Scheme II. As shown in Reaction Scheme II, these acrylic esters and acids are synthesized from t-butyl-acetoacetic ester by alkylation with the appropriate $R_1 X$ wherein X is a good leaving group such as, for example, bromo or iodo, followed by base catalyzed condensation with formaldehyde and cleavage of the acetyl function with concurrent loss of water to yield Compound II.

Activation of amino acid esters, $HN(R_3)$—$CH(R_4)$—$CO_2R$, with phosgene is accomplished in an inert solvent such as teterahydrofuran (THF) in the presence of aprotic basic catalysis to yield Compound IV. Compound IV is then condensed with Compound III, again in an inert solvent in the presence of a base such as for example, triethylamine (TEA), to afford Compound I or a protected form of Compound I.

Alternatively, Compound III can be reacted with phosgene and subsequently condensed with an amino acid ester, $HN(R_3)$—$CH(R_4)$—$CO_2R$, as described in Example 10 hereinbelow.

If desired, protecting groups can then be removed employing methods known to those skilled in the art. For example, benzyl ester protecting groups can be cleaved by hydrogenation in the presence of a palladium-on-charcoal catalyst to afford the corresponding acids.

If also desired, diesters can be made from compounds of Formula I where R=H by Fisher esterification involving the desired alcohol with acid catalysis.

In compounds of Formula I, the carbon atoms to which $R_1$ and $R_4$ are attached are asymmetric; therefore, diastereomers of Formula I are possible. Starting materials III and amino acids $HN(R_3)$—$CH(R_4)$—$CO_2R$ can be employed as racemates or as pure enantiomers or diastereomers in the synthesis of compounds of Formula I. When mixtures of diastereomeric products result from such syntheses, they can be separated to afford the preferred diastereomers if desired such as, for example, by chromatographic or fractional crystallization methods.

In general, the carbon atom to which $R_4$ is attached is preferred in the L-aminoacid configuration. Designation of the preferred, absolute configuration at the carbon bearing $R_1$ varies with the substitution pattern in $R_1$.

The compounds of this invention form salts with various inorganic and organic acids and bases which are also within the scope of the invention. Such salts include ammonium salts, alkali metal salts like sodium and potassium salts (which are preferred), alkaline earth metal salts like the calcium and magnesium salts, salts with organic bases; e.g., dicyclohexylamine salts, N-methyl-D-glucamine, salts with amino acids like arginine, lysine, and the like. Also salts with organic and inorganic acids may be prepared, when one of the substituent R groups in compounds of Formula I contains a basic group. Said salts such as HCl, HBr, $H_2SO_4$, $H_3PO_4$, methanesulfonic, toluensulfonic, maleic, fumaric, camphorsulfonic are then possible. The nontoxic physiologically acceptable salts are preferred, although other salts are also useful, e.g., in isolating or purifying the product.

The salts may be formed by conventional means as by reacting the free acid or free base forms of the product with one or more equivalents of the appropriate base or acid in a solvent or medium in which the salt is insoluble, or in a solvent such as water which is then removed in vacuo or by freeze-drying or by exchanging the cations of an existing salt for another cation on a suitable ion exchange resin.

The compounds of this invention inhibit angiotensin converting enzyme and thus block conversion of the decapeptide angiotensin I to angiotensin II. Angiotensin II is a potent pressor substance. Thus, blood-pressure lowering can result from inhibition of its biosynthesis especially in animals and humans whose hypertension is angiotensin II related. Furthermore, converting enzyme degrades the vasodepressor substance, bradykinin. Therefore, inhibitors of angiotensin converting enzyme may lower blood-pressure also by potentiation of bradykinin. Although the relative importance of these and other possible mechanisms remains to be established, inhibitors of angiotensin converting enzyme are effective antihypertensive agents in a variety of animal models and are useful clinically, for example, in many human patients with renovascular, malignant and essential hypertension. See, for example, D. W. Cushman et al., *Biochemistry* 16, 5484 (1977).

The evaluation of converting enzyme inhibitors is guided by in vitro enzyme inhibition assays. For example, a useful method is that of Y. Piquilloud, A. Reinharz and M. Roth, *Biochem. Biophys. Acta,* 206, 136 (1970) in which the hydrolysis of carbobenzyloxyphenylalanylhistidinylleucine is measured. In vivo evaluations may be made, for example, in normotensive rats challenged with angiotensin I by the technique of J. R. Weeks and J. A. Jones, *Proc. Soc. Exp. Biol. Med.,* 104, 646 (1960) or in a high renin rat model such as that of S. Koletsky et al., *Proc. Soc. Exp. Biol. Med.* 125, 96 (1967).

Thus, the compounds of this invention are useful as antihypertensives in treating hypertensive mammals, including humans, and they can be utilized to achieve the reduction of blood pressure by formulating in compositions such as tablets, capsules or elixirs for oral administration or in sterile solutions or suspensions for parenteral administration. The compounds of this invention can be administered to patients in need of such treatment in a dosage range of 5 to 250 mg per patient generally given several times, thus giving a total daily dose of from 5 to 1000 mg per day. The dose will vary depending on severity of disease, weight of patient and other factors which a person skilled in the art will recognize.

Also, the compounds of this invention may be given in combination with diuretics or other antihypertensives. Typically these are combinations whose individual per day dosages range from one-fifth of the minimally recommended clinical dosages to the maximum recommended levels for the entities when they are given singly. To illustrate these combinations, one of the antihypertensives of this invention effective clinically in the range 15-200 milligrams per day can be effectively combined at levels ranging from 3-200 milligrams per day with the following antihypertensives and diuretics in dose ranges per day as indicated:

hydrochlorothiazide (10-100 mg),
  pivaloyloxyethyl ester of methyldopa (30-1000 mg),
  indacrinone (25-150 mg),
  timolol (5-60 mg), 4-{3-{[2-(1-hydroxycyclohexyl)ethyl]-4-oxo-2-thiazolidinyl}propyl}-benzoic acid (10-100 mg), and methyldopa (65-2000 mg).

In addition, the triple drug combinations of hydrochlorothiazide (10-100 mg) plus amiloride (5-20 mg) plus converting enzyme inhibitor of this invention (3-200 mg) or hydrochlorothiazide (10-100 mg) plus timolol (5-60 mg) plus the converting enzyme inhibitor of this invention (3-200 mg) are effective combinations to control blood pressure in hypertensive patients.

The above dose ranges will be adjusted on a unit basis as necessary to permit divided daily dosage. Also, the dose will vary depending on the severity of the disease, weight of patient and other factors which a person skilled in the art will recognize.

Typically the combinations shown above are formulated into pharmaceutical compositions as discussed below.

About 5 to 250 mg of a compound or mixture of compounds of Formula I or a physiologically acceptable salt thereof is compounded with a physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage is obtained in the range(s) indicated above.

Illustrative of the adjuvants which may be incorporated in tablets, capsules and the like are the following: a binder such as gum tragacanth, acacia, corn starch or gelatin; an excipient such as microcrystalline cellulose; a disintegrating agent such as corn starch, pregelatinized starch, alginic acid and the like; a lubricant such as magnesium stearate; a sweetening agent such as sucrose, lactose or saccharin; a flavoring agent such as peppermint, oil of wintergreen or cherry. When the dosage unit form is a capsule, it may contain, in addition to materials of the above type, a liquid carrier such as fatty oil. Various other materials may be present as coatings or to otherwise modify the physical form of the dosage unit. For instance, tablets may be coated with shellac, sugar or both. A syrup or elixir may contain the active compound, sucrose as a sweetening agent, methyl and propyl parabens as preservatives, a dye and a flavoring such as cherry or orange flavor.

Sterile compositions for injection can be formulated according to conventional pharmaceutical practice by dissolving or suspending the active substance in a vehicle such as water for injection, a naturally occurring vegetable oil like sesame oil, coconut oil, peanut oil, cottonseed oil, etc. or a synthetic fatty vehicle like ethyl oleate or the like. Buffers, preservatives, antioxidants and the like can be incorporated as required.

The following examples are illustrative of the invention and constitute especially preferred embodiments. The biologically more active diastereomers of these examples are isolated by column chromatography or fractional crystallization. All temperatures are in degrees Celsius. The H'NMR data are given in ppm with tetramethylsilane as the standard.

EXAMPLE 1 t-Butyl 2-(2-phenylethyl)-3-oxobutyrate

Sodium (2.3 g; 0.10 mol) was allowed to react with dry ethanol (50 ml) under nitrogen. The resulting clear solution was cooled (ice bath) and t-butyl acetoacetate (15.8 g; 0.10 mol) was added during 10 minutes with stirring. After 10 minutes, 2-(bromoethyl)benzene (18.5 g; 0.10 mol) was added during 30 minutes. The resulting solution was heated at reflux for 4 hours, then cooled and filtered. After concentration, the residue was partitioned between water and ether, and the ether layer was dried ($MgSO_4$) and concentrated. Distillation of the residue gave 21.0 g (0.080 mol; 80%) of the title product; bp 110°-120° (0.3 mm). NMR ($CDCL_3$); 1.45 (9H,s), 2.17 (3H,s), 1.8-2.4 (2H,m), 2.5-2.7 (2H,m); 3.28 (1H,J=7); 7.2-7.4 (5H, broad s). MS (m/e); 262 (M+).

EXAMPLE 2 t-Butyl-2-methylene-4-phenylbutyrate

A solution of lithium diisopropylamide in tetrahydrofuran was prepared by addition of n-butyllithium (4.2 ml, 11 mmol) to a solution of diisopropylamine (1.1 g, 11 mmol) in anhydrous THF (22 ml) cooled to −78° (dry-ice acetone bath). After additon of t-butyl-2-(2-phenylethyl)-3-oxobutyrate (2.62 g, 10 mmol), the mixture was stirred for 10 minutes, then dry paraformaldehyde (1.4 g) was added all at once. The mixture was allowed to warm to room temperature, stirred for one hour at this temperature, then heated at reflux for one hour. The mixture was cooled, filtered, and concentrated, and the residue was purified by chromatography on neutral alumina, giving the title product (0.62 g, 2.7 mmol, 27%) as a colorless oil. NMR ($CDCl_3$); 1.48 (9H,s), 2.3-3.0 (4H,m), 5.2 (1H, broad s), 6.05 (1H,d,J=1 Hz), 7.13 (5H,s). IR ($CHCl_3$); 1700, 1630, 1590 $cm^{-1}$. MS (m/e); 232 (M+).

EXAMPLE 3

N-[3-(t-Butyl-2-(2-phenethyl)proprionate)]N-ethylamine

A ten fold excess of ethyl amine was added to a solution of 1.66 g (7.16 mmol) of t-butyl-2-methylene-4-phenylbutyrate in 25 ml of anhydrous ethanol. After stirring for 5 days at room temperature, the reaction was concentrated to give 1.94 g (98%) of the crude product as an oil. The desired title product can be purified by chromatography on silica gel (ethylacetate, $R_f$ 0.4) or used crude for subsequent reaction. NMR ($CDCl_3$); 7.2 (5H,s), 2.6 (m, 8H), 1.9 (m, 2H), 1.5 (s, 9H), 1.1 (t, 3H).

EXAMPLE 4 t-Butyl N-(2-t-butoxycarbonyl-4-phenyl butyl)-N-ethylaminocarbonyl-L-prolinate

A. t-Butyl N-chlorocarbonyl-L-prolinate

A solution of 0.961 g (5.62 mmol) of t-butyl prolinate and 0.80 ml (5.76 mmol) of triethylamine in 4.2 ml of dry tetrahydrofuran was added dropwise to a stirring solution of phosgene in toluene (12.5%, 5.9 ml, 6.74 mmol) precooled to 0°. The reaction was allowed to warm to room temperature and stirred for an additional hour. After filtering and concentrating, a yellow oil was obtained which was used directly for the next step, B.

B. t-Butyl N-(2-t-butoxycarbonyl-4-phenyl butyl)-N-ethylaminocarbonyl-L-prolinate A solution of 0.650 g (2.79 mmol) of t-butyl N-chlorocarbonyl-L-prolinate in 3.5 ml of dry tetrahydrofuran was added to a solution of 0.650 g (2.35 mmol) of N-[3-(t-butyl 2-(2-phenethyl)propionate)]-N-ethyl amine in 3.5 ml of dry tetrahydrofuran at room temperature. Subsequently, 0.59 ml (4.19 mmol) of triethylamine was added. After 2.5 hours, the reaction was filtered and the filtrate diluted with ether. After washing with water (2X), brine (1X), drying ($MgSO_4$), and concentrating, 1.24 g (100%) of a yellow oil was obtained. The diastereomers of the product were separated and purified by chromatography on a medium pressure liquid chromatograph (silica gel, 7/3—hexanes/ethyl acetate, $R_f$~0.4) to give a total of 0.569 g of product (51%) in a diasteromer ratio of ca. 1:1.

Isomer A (first isomer off the column); MS (m/e); 474 ($M^+$), combustion analysis; theory: C, 68.33; H, 8.92; N, 5.90; found: C, 68.25; H, 8.91; N, 5.73. IR (neat); 1710, 1640 $cm^{-1}$.

Isomer B (second isomer off the column); MS (m/e); 474 ($M^+$) combustion analysis; theory: C, 68.33; H, 8.92; N, 5.90; found: C, 67.98; H, 9.00; N, 5.70. IR (neat); 1710, 1640 $cm^{-1}$.

Isomers A and B were carried on separately as described below in Example 5.

EXAMPLE 5

N-(2-Carboxy-4-phenylbutyl)-N-ethylaminocarbonyl-L-proline

A solution of 0.161 g (0.339 mmol) of t-butyl-N-(2-t-butoxycarbonyl-4-phenylbutyl)-N-ethylaminocarbonyl-L-prolinate (isomer A from Example 4 above) in 3 ml of trifluoroacetic acid was prepared at 0° then allowed to warm to room temperature and then stirred for 4.5 hours. After concentrating, saturated $NaHCO_3$ was added followed by ether. After mixing and removing the ether layer, the aqueous layer was acidified with 10% HCl and extracted with ether. The combined ether extracts were dried ($MgSO_4$) and concentrated to give 0.130 g (100%) of the diacid as a viscous oil. NMR ($CDCl_3$); 7.2 (s, 5H), 4.5 (m, 1H), 3.4 (m,7H), 2.7 (t, 2H), 2.0 (m, 6H), 1.2 (t, 3H). MS and (m/e); 362 ($M^+$). The same procedure was applied to isomer B to afford the corresponding isomeric diacid. NMR ($CDCl_3$); same as isomer A.

EXAMPLE 6

N-[3-(t-Butyl-2-(2-phenethyl)propionate)]-N-methylamine

A solution of t-butyl-2-methylene-4 phenyl butyrate (0.62 g; 2.7 mmol) in ethanol (absolute; 5 ml) was added to a solution of ethanol (10 ml) pre-saturated with methylamine gas. The resulting solution was allowed to stand for 4 days and was then concentrated. Purification of the residue on silica gel provided the title product (0.55 g, 2.1 mmol, 77%). NMR ($CDCl_3$); 1.45 (9H, s), 1.7–2.0 (2H, m), 2.03 (3H, s), 2.4–3.0 (5H, m), 7.3 (5H, s). IR ($CHCl_3$); 1725 $cm^{-1}$. MS (m/e); 263 ($M^+$).

EXAMPLE 7 t-Butyl N-(2-t-butoxycarbonyl-4-phenylbutyl)-N-methylaminocarbonyl-L-prolinate

The amino ester of Example 6 (0.44; 1.68 mmol) and t-butyl-N-chlorocarbonyl-L-prolinate (from Example 4) (0.47 g, 2.0 mmol) were used as described in Example 4 to prepare, after chromatography on silica gel, the title urea compounds. (0.56 g; 1.25 mmol; 74%) as a 1:1 mixture of diastereomers. NMR ($CDCl_3$); 1.43 (9H, s), 1.7–2.3 (6H, m), 2.5–2.9 (2H, m), 2.85 (3H, s), 3.2–3.8 (5H, m), 4.3–4.6 (1H, m), 7.1 (5H, broad s). MS (m/e); 460 ($M^+$).

EXAMPLE 8

N-(2-Carboxy-4-phenylbutyl)-N-methylaminocarbonyl-L-proline

A solution of the diester product from Example 7 (0.17 g; 0.37 mmol) in trifluoroacetic acid (5 ml) was allowed to stand for 5 hours. The mixture was then concentrated and the residue purified on a Sephadex LH-20 column (in methanol) giving the title product (70 mg, 0.20 mmol, 54%) as a 1:1 mixture of diastereomers. TLC (silica gel; EtOAc, Pyr, $H_2O$, AcOH, 20:5:1:1) $R_f$=0.4. NMR ($CDCl_3$); 1.8–2.3 (6H, m); 2.6–3.0 (2H, m), 2.90 (3H, s), 3.3–3.7 (5H, m), 4.4–4.7 (1H, m), 7.3 (5H, broad s). MS (m/e); 492 ($M^+$, bis-trimethylsilyl).

EXAMPLE 9

N-[3-(t-Butyl-2-(2-phenethyl)propionate]-N-isopropylamine

A twenty fold excess of isopropylamine was added to a solution of 0.50 g (2.16 mmol) of t-butyl-2-methylene-4-phenylbutyrate in 8 ml of anhydrous ethanol. After stirring 15 days at room temperature, the reaction was concentrated to give a clear oil. NMR ($CDCl_3$); 7.2 (5H, s), 2.7 (7H, m), 1.9 (2H, m), 1.5 (9H, s), 1.0 (6H, d).

EXAMPLE 10

Methyl-N-(2-t-butoxycarbonyl-4-phenylbutyl)-N-isopropylaminocarbonyl-L-tryptophanate A. N-(2-t-butoxycarbonyl-4-phenylbutyl)-N-chlorocarbonyl-N-isopropylamine A solution of 0.300 g (1.03 mmol) of N-[3-(t-butyl-2-(2-phenethyl)propionate]-N-isopropylamine and 0.15 ml (1.08 mmol) of triethylamine in 0.77 ml of dry tetrahydrofuran was added dropwise to a stirring solution of phosgene in toluene (12.5%, 1.08 ml, 1.23 mmol) precooled to 0°. The reaction was allowed to warm to room temperature and stirred an additional hour. The reaction was concentrated, diluted with methylene chloride, filtered and concentrated again to give 0.331 g of a solid. This product was used directly for the next step without purification.

B. Methyl-N-(2-t-butoxycarbonyl-4-phenylbutyl)-N-isopropylaminocarbonyl-L-tryptophanate A solution of the crude N-(2-t-butoxycarbonyl-4-phenylbutyl)-N-chlorocarbonyl-N-isopropylamine (0.331 g, 0.94 mmol) in 2.3 ml of dry THF was added to a solution of 0.212 g (0.834 mmol) of L-tryptophane methyl ester and 0.31 ml (2.22 mmol) of triethylamine in 1.3 ml of dry tetrahydrofuran at 0°. The reaction was allowed to warm to room temperature and stirred overnight. The reaction was then filtered, diluted with ether, washed with water (2X), brine (1X), dried (MgSO$_4$) and concentrated to give 0.413 g of an oil. The product was purified by preparative thin layer chromatography over silica gel using a 2/1-ethyl acetate/hexanes developing solution. The product diastereomers ($R_f \sim 0.6$) were isolated as 0.329 g (74%) of a thick yellow oil. MS (m/e); 535 (M+). NMR (CDCl$_3$); 6.8–7.5 (11H, m), 5.4 (1H, m), 4.7 (1H, m), 4.2–1.3 (22H, m), 1.0 (6H, d).

EXAMPLE 11

N-(2-Carboxy-4-phenylbutyl)-N-isopropylaminocarbonyl-L-tryptophan

A solution of 0.270 g (0.505 mmol) of methyl-N-(2-t-butoxycarbonyl-4-phenylbutyl)-N-isopropylaminocarbonyl-L-tryptophanate in 6 ml of trifluoroacetic acid was prepared at 0° and stirred for 3 hours. After concentrating, the residue was dissolved in a solution of 0.121 g (3.03 mmol) of sodium hydroxide, 5 ml of methanol and 4.5 ml of water. The resulting reaction was stirred at room temperature overnight then diluted with 20 ml of water and acidified with 10% hydrochloric acid. The product was extracted with ether (2X) then washed with water (2X), brine (1X), dried (MgSO$_4$) and concentrated to give 0.228 g of an oil. The product diastereomers were purified by chromatography on a Sephadex LH-20 column (using methanol) to give 0.124 g (53%) of an oil. MS (m/e); silylated); 332, 202, 91, 73. NMR (CDCl$_3$); 8.8 (1H, broad s), 7.1 (10H, m), 5.8 (1H, broad s), 5.2 (1H, broad s), 4.6 (1H, broad s), 4.0–0.6 (15H, m).

EXAMPLE 12

Ethyl-N-(2-t-butoxycarbonyl-4-phenylbutyl)-N-ethylaminocarbonyl-L-1,2,3,4-tetrahydro-3-isoquinolinecarboxylate A. Ethyl-N-chlorocarbonyl-L-1,2,3,4-tetrahydro-3-isoquinolinecarboxylate Ethyl-L-1,2,3,4-tetrahydroisoquinoline-3-carboxylate [S. Yamoda and T. Kunieda, *Chem. Pharm. Bull.*, 15, 490 (1967)] was substituted for t-butyl prolinate in Example 4A to obtain the title compound as a yellow oil which was used directly for the next step, B.

B. Ethyl-N-(2-t-butoxycarbonyl-4-phenylbutyl)-N-ethylaminocarbonyl-L-1,2,3,4-tetrahydro-3-isoquinolinecarboxylate Ethyl-N-chlorocarbonyl-L-1,2,3,4-tetrahydro-3-isoquinolinecarboxylate was substituted for t-butyl-N-chlorocarbonyl-L-prolinate in Example 4B. The product was purified by chromatography on a medium pressure liquid chromatograph (silica gel, 7/3-hexanes/ethyl acetate) to give a 54% yield of the title compound as a ca. 1/1 mixture of diastereomers. MS (m/e); 508 (M+), 435 (M-CO$_2$Et)+. NMR (CDCl$_3$); 7.1 (9H, m), 4.8 (1H, dd), 4.5 (2H, s), 4.1 (2H, g), 3.8–1.6 (11H, m), 1.5 (9H, s), 1.2 (6H, t).

EXAMPLE 13

N-(2-Carboxy-4-phenylbutyl)-N-ethylaminocarbonyl-L-1,2,3,4-tetrahydro-3-isoquiolinecarboxylic acid A solution of 0.346 g (0.681 mmol) of ethyl-N-(2-t-butoxycarbonyl-4-phenylbutyl)-N-ethylaminocarbonyl-L-1,2,3,4-tetrahydro-3-isoquinolinecarboxylate in 5 ml of trifluoroacetic acid was prepared at 0° and stirred at room temperature for 2 hours. After concentrating, the residue was dissolved in a solution of 0.163 g (4.08 mmol) of sodium hydroxide, 3.5 ml of water and 2.5 ml of methanol. The resulting reaction was stirred at room temperature overnight then diluted with 30 ml of water. After washing with ether (2X), the aqueous layer was acidified with 10% hydrochloric acid and the product extracted with ether. The ether extracts were washed with brine (1X), dried (MgSO$_4$) and concentrated to give 0.277 (96%) of white solid. MS (m/e, silylated); 568 (M+), 553 (M-CH$_3$)+. NMR (CDCl$_3$; 7.1 (9H, s), 4.6 (3H, m), 3.6–2.3 (9H, m), 1.9 (2H, m), 1.1 (3H, m).

EXAMPLE 14

N-Benzyloxycarbonyl-N'-[3-(t-butyl-2-(2-phenethyl)-propionate)]-1,4-butanediamine A ten fold excess of N-benzyloxycarbonyl-1,4-butanediamine [E. Walchli-Schaer and C. Eugster, *Helvetica Chimica Acta*, 61, 928 (1978)] was added to a solution of 0.180 g (0.690 mmol) of t-butyl-2-methylene-4-phenylbutyrate in 3.2 ml of absolute ethanol. After stirring at room temperature for 3 days, 4 ml of absolute ethanol was added and the reaction heated to 60° for 11 days. The reaction was then concentrated and the residue diluted with methylene chloride. After standing at room temperature for a day, a white precipitate appeared which was removed by filtration. The product was isolated from the remaining material by chromatography on a Sephadex LH-20 column (using methanol) to give 0.14 g (44%) of the product in reasonable purity. MS (m/e); 454 (M+), 381 (M-t-butoxy)+. NMR (CDCl$_3$); 7.2 (10H, m), 5.6 (1H, broad s), 5.0 (2H, s), 3.4–1.6 (16H, m), 1.5 (9H, s).

EXAMPLE 15 t-Butyl-N-benzyloxycarbonyl-N'-[2-t-butoxycarbonyl-4-phenylbutyl]-N'-(4-aminobutyl)-aminocarbonyl-L-prolinate A solution of 82 mg (0.35 mmol) of t-butyl-N-chlorocarbonyl-L-prolinate (prepared as in example 4A) in 1.0 ml of dry tetrahydrofuran was added to a solution of 132 mg (0.29 mmol) of N-benzyloxycarbonyl-N'-[3-(t-butyl-2-(2-phenethyl)propionate)]-1,4-butane diamine in 1.0 ml of dry tetrahydrofuran at room temperature. Subsequently, 0.071 ml (0.53 mmol) of triethylamine was added. After 1 hour, the reaction was filtered and the filtrate diluted with ether and methylene chloride. After washing with water (2X), brine (1X), drying (MgSO₄) and concentrating, 180 mg of an oil was obtained. The diastereomers of the product were purified by preparative thin layer chromatography over silica gel using a 1/1-ethyl acetate/hexanes developing solution. The product diastereomers ($R_f$~0.4) were isolated as 70 mg (37%) of an oil. MS (m/e); 651 (M+), 578 (M-t-butoxy)+. NMR (CDCl₃); 7.2 (10H, m), 5.4 (1H, broad s), 5.0 (2H, s), 4.4 (1H, m), 3.8–1.6(19H, m), 1.5 (18H, s).

EXAMPLE 16

N-Benzyloxycarbonyl-N'-(2-carboxy-4-phenylbutyl)-N'-(4-aminobutyl)-aminocarbonyl-L-proline A solution of 70 mg of t-butyl-N-benzyloxycarbonyl-N'-[2-t-butoxycarbonyl-4-phenylbutyl]-N'-(4-aminobutyl)-aminocarbonyl-L-prolinate in 4 ml of trifluoroacetic acid was prepared and stirred for 2.5 hours at room temperature. After concentrating, the residue was dissolved in ethyl acetate and washed with water (3X), dried (MgSO₄) and concentrated to give 40 mg (69%) of an oil. NMR (CDCl₃); 7.7 (3H, broad s), 7.2 (10H, m), 5.0 (2H, s), 4.4 (1H, m), 3.7–1.0 (21H, m).

EXAMPLE 17

N-(2-Carboxy-4-phenylbutyl)-N-(4-aminobutyl)aminocarbonyl-L-proline

A solution of 20 mg (0.04 mmol) of N-benzyloxycarbonyl-N'-(2-carboxy-4-phenylbutyl)-N'-(4-aminobutyl)-aminocarbonyl-L-proline in 6 ml of a 3/1-absolute ethanol/acetic acid mixture was hydrogenated over 20 mg of 10% palladium on carbon at 40 psig (Parr hydrogenator) and room temperature overnight. The reaction was filtered and concentrated then diluted with water and absorbed on a Dowex 50W (H+) resin (3 ml). After washing the column with water, the product was eluted with 2% pyridine/water. The eluent was concentrated then freeze dried to give 5 mg (33%) of the title compound in good purity [one spot on TLC, $R_f$=0.65 (silica gel, 1/1/1/1-water/ethyl acetate/n-butanol/acetic acid)]. MS (m/e, silylated); 693 (M+, tetrasilylated), 678 (M, tetrasilylated-CH₃)+, 621 (M+, trisilylated), 606 (M, trisilylated-CH₃)+, 576 (M, tetrasilyl-CO₂SiMe₃)+. NMR (CD₃OD); 7.2 (5H, s), 4.4 (1H, m), 3.7–1.4 (25H, m).

EXAMPLE 18 t-Butyl-N-(2-ethoxycarbonyl-4-phenylbutyl)-N-ethylaminocarbonyl-L-prolinate

The title compound can be obtained by substituting ethyl acetoacetate for t-butyl acetoacetate in Example 1 and following the experimental procedures of Examples 1, 2, 3 and 4.

EXAMPLE 19

N-(2-ethoxycarbonyl-4-phenylbutyl)-N-ethylaminocarbonyl-L-proline

The title compound can be obtained by substituting t-butyl-N-(2-ethoxycarbonyl-4-phenylbutyl)-N-ethylaminocarbonyl-L-prolinate for t-butyl-N-(2-t-butoxycarbonyl-4-phenylbutyl)-N-ethylaminocarbonyl-L-prolinate in Example 5.

EXAMPLE 20

Ethyl-N-(2-ethoxycarbonyl-4-phenylbutyl)-N-ethylaminocarbonyl-L-prolinate

A solution of N-(2-carboxy-4-phenylbutyl)-N-ethylaminocarbonyl-L-proline in absolute ethanol was saturated with hydrogen chloride gas at 0°. The reaction was allowed to warm to room temperature and stirred overnight with a drying tube attached to the flask. The reaction was then degassed with a stream of nitrogen and concentrated. The residue was diluted with ether and washed with saturated sodium bicarbonate (1X), water (1X), brine, (1X), dried (MgSO₄) and concentrated to give the title compound. This material can be further purified by chromatography if desired.

EXAMPLE 21

Additional Compounds of Formula I

Amino acids of formula

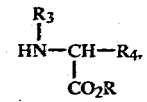

particularly useful in the synthesis of products of Formula I, are listed in Table I. It is also possible to synthesize t-butyl-2-methylene-4-phenylbutyrate, t-butyl-2-methylene-4-(1-naphthyl)butyrate, t-butyl-2-methylene-4-(2-thienyl)butyrate and t-butyl-4-(4-isoquinolinyl)-2-methylenebutyrate by methods illustrated or described in this invention. These starting materials, when reacted with methylamine, ethylamine, N-benzyloxycarbonyl-1,4-butanediamine or ammonia, can afford intermediates of Formula III listed in Table II. As taught in the Examples above, amino acids in Table I as esters may be reacted with phosgene in an inert solvent and the resultant intermediates coupled with intermediates listed in Table II to afford, after removal of protecting groups, further products of Formula I listed in Table III. Diesters are prepared by Fischer esterification according to Example 20.

TABLE I

Amino Acids of the Formula:

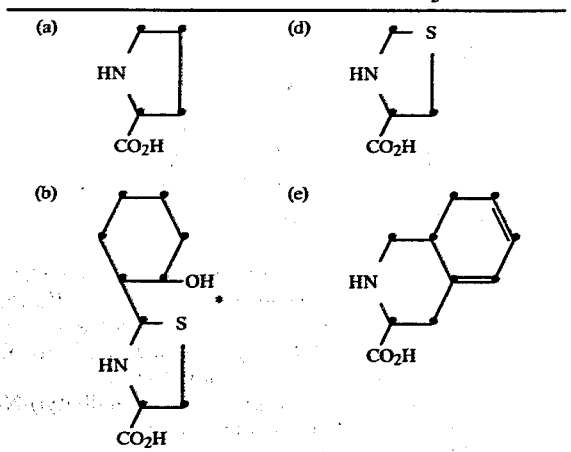

TABLE I-continued

Amino Acids of the Formula: $\underset{\underset{CO_2R}{|}}{HN-\overset{\overset{R_3}{|}}{CH}-R_4}$ (c) [structure: HN-CH2-CH(OCH3)-CO2H, with OCH3 wedge bond]

(f) [structure: 2-methylphenyl-CH2-CH(NH)-CO2H]

*In this case the coupling is accomplished by reacting phosgene with the Formula III intermediate and subsequent reaction with this amino ester as illustrated in Example 10.

TABLE II

Intermediates of the Formula: $\underset{\underset{CO_2R}{|}}{\overset{\overset{R_1}{|}}{CH}-CH_2-\overset{\overset{R_2}{|}}{NH}}$ (III)

(g) [structure: Ph-CH2CH2-CH(CO2Bu^t)-CH2NH2]

(h) [structure: naphthyl-CH2-CH2-CH(CO2Bu^t)-CH2-NH-CH3]

(i) [structure: isoquinolinyl-CH2-CH2-CH(CO2Bu^t)-CH2-NH-CH2CH3]

(j) [structure: thienyl-CH2-CH2-CH(CO2Bu^t)-CH2-NH-(CH2)4-NH-Cbz]

TABLE III

Additional Compounds of Formula I:

$\underset{\underset{CO_2R}{|}}{\overset{\overset{R_1}{|}}{CH}}-CH_2-\overset{\overset{R_2}{|}}{N}-CON-\underset{\underset{CO_2R}{|}}{\overset{\overset{R_3}{|}}{CH}-R_4}$ (k) [structure with naphthyl-CH2-CH(CO2H)-CH2-N(CH3)-CON-cyclic-CO2H]

(l) [structure: Ph-CH2-CH2-CH(CO2H)-CH2-NHCON-CH(aryl-OH)-S-cyclic, CO2H]

(m) [structure: Ph-CH2-CH2-CH(CO2Et)-CH2-NHCON-CH(aryl-OH)-S-cyclic, CO2Et]

(n) [structure: isoquinolinyl-CH2-CH2-CH(CO2Et)-CH2-N(CH2CH3)-CON-CH(CH3)-CO2Et]

(o) [structure: thienyl-CH2-CH2-CH(CO2H)-CH2-N-CON-CH((CH2)4NH2)-S-cyclic, CO2H]

(p) [structure: Ph-CH2-CH2-CH(CO2Et)-CH2-NH-CON-CH2-aryl-CO2Et]

TABLE III-continued
Additional Compounds of Formula I:

$$\underset{CO_2R}{\overset{R_1}{CH}}-CH_2-\underset{}{\overset{R_2}{N}}-CON-\underset{CO_2R}{\overset{R_3}{CH}}-R_4$$

(q) [structure: naphthyl-CH2-CH(CO2H)-CH2-N(CH3)-CON-proline-like ring with OCH3 and CO2H]

(r) [structure: isoquinoline-CH2-CH(CO2H)-CH2-N(CH3)-CON-CH(CH2-phenyl)-CO2H]

What is claimed is:

1. A compound of the formula:

$$\underset{CO_2R}{\overset{R_1}{CH}}-CH_2-\overset{R_2}{N}-CON-\underset{CO_2R}{\overset{R_3}{CH}}-R_4$$

wherein:
R is the same or different and is hydrogen, loweralkyl, aralkyl;
$R_1$ is alkyl of from one to ten carbon atoms which include branched, cyclic, and unsaturated alkenyl and alkynyl groups;
substituted alkyl of from one to six carbon atoms and the substituent is amino, arylthio, aryloxy, hydroxy, arylamino, loweralkanoylamino, and aroylamino;
aralkyl optionally substituted by halo, loweralkyl, hydroxy, alkoxy, and amino groups wherein the alkyl groups contain from one to six carbon atoms;
$R_2$ is hydrogen, alkyl of from one to six carbon atoms optionally substituted by amino, loweralkylamino, arylamino, loweralkanoylamino, aroylamino, or aryl groups;
$R_3$ and $R_4$ may be connected together to form a proline moiety; and,
a pharmaceutically acceptable salt thereof.

2. A compound of the formula:

$$\underset{CO_2R}{\overset{R_1}{CH}}-CH_2-\overset{R_2}{N}-CON-\underset{CO_2R}{\overset{R_3}{CH}}-R_4$$

wherein:
R is the same or different and is hydrogen, loweralkyl, aralkyl;
$R_1$ is alkyl of from one to six carbon atoms optionally substituted by amino, hydroxyl, loweralkanoylamino, aroylamino, aryloxy;
aralkyl, optionally substituted by halo, loweralkyl, hydroxy, alkoxy, and amino groups wherein the alkyl groups contain from one to six carbon atoms;
$R_2$ is hydrogen or alkyl of from one to six carbon atoms optionally substituted by amino;
$R_3$ and $R_4$ may be connected together to form a proline moiety; and,
a pharmaceutically acceptable salt thereof.

3. A compound of the formula:

$$\underset{CO_2R}{\overset{R_1}{CH}}-CH_2-\overset{R_2}{N}-CON-\underset{CO_2R}{\overset{R_3}{CH}}-R_4$$

wherein:
R is the same or different and is hydrogen, loweralkyl, aralkyl;
$R_1$ is alkyl of from one to six carbon atoms optionally substituted by amino, hydroxyl, loweralkanoylamino, aroylamino, aryloxy;
aralkyl, optionally substituted by halo, loweralkyl, hydroxy, alkoxy, and amino groups wherein the alkyl groups contain from one to six carbon atoms;
$R_2$ is hydrogen or alkyl of from one to six carbon atome optionally substituted by amino, groups;
$R_3$ and $R_4$ are joined through the nitrogen and carbon atoms to which they are respectively attached to form a five membered ring having the formula:

$$\begin{array}{c} Ar \\ \diagup \\ N \qquad X \\ \diagdown \\ (CH_2)_l \\ | \\ CO_2H \end{array}$$

wherein X is $CH_2$, CHOH, $CHOCH_3$; l is one; and Ar is phenyl, 2-hydroxyphenyl, or naphthyl; or a pharmaceutically acceptable salt thereof.

4. A compound of the formula:

$$\underset{CO_2R}{\overset{R_1}{CH}}-CH_2-\overset{R_2}{N}-CON-\underset{CO_2R}{\overset{R_3}{CH}}-R_4$$

wherein:
R is the same or different and is hydrogen or loweralkyl;
$R_1$ is aralkyl optionally substituted by halo, loweralkyl, hydroxy, alkoxy, and amino groups wherein the alkyl groups contain one to four carbon atoms;
$R_2$ is hydrogen, alkyl of from one to six carbon atoms, or amino substituted alkyl of from one to six carbon atoms;
$R_3$ and $R_4$ are joined through the nitrogen and carbon atoms to which they are respectively attached to form a proline ring structure;

or a pharmaceutically acceptable salt thereof.

5. A compound of claim 4 which is: N-(2-carboxy-4-phenylbutyl)-N-ethylaminocarbonyl-L-proline.

6. A compound of claim 4 which is: N-(2-carboxy-4-phenylbutyl)-N-methylaminocarbonyl-L-proline.

7. A compound of claim 4 which is: N-[(2-ethoxycarbonyl)-4-phenylbutyl]-N-ethylaminocarbonyl-L-proline.

8. A compound of claim 4 which is: ethyl N-[(2-ethoxycarbonyl)-4-phenylbutyl]-N-ethylaminocarbonyl-L-prolinate.

9. A compound of claim 4 which is: N-(2-carboxy-4-phenylbutyl)-N-(4-aminobutyl)-aminocarbonyl-L-proline.

10. A pharmaceutical composition useful in the treatment of hypertension which comprises a pharmaceutically acceptable carrier and a pharmaceutically effective amount of a compound of the formula:

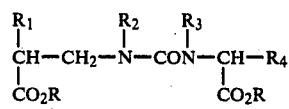

wherein:
R is the same or different and is hydrogen, loweralkyl, aralkyl;
$R_1$ is alkyl of from one to ten carbon atoms which include branched, cyclic, and unsaturated alkenyl and alkynyl groups; substituted alkyl of from one to six carbon atoms and the substitutent is amino, arylthio, aryloxy, hydroxy, arylaminio, loweralkanoylamino, and aroylamino;
aralkyl optionally substituted by halo, loweralkyl, hydroxy, alkoxy, and amino groups wherein the alkyl groups contain from one to six carbon atoms;
$R_2$ is hydrogen, alkyl of from one to six carbon atoms optionally substituted by amino, loweralkylamino, arylamino, loweralkanoylamino, aroylamino; or aryl groups;
$R_3$ and $R_4$ may be connected together to form a proline moiety; and
a pharmaceutically acceptable salt thereof.

11. The composition of claim 10 wherein:
R is the same or different and is hydrogen, loweralkyl, aralkyl;
$R_1$ is alkyl of from one to six carbon atoms optionally substituted by amino, hydroxyl, loweralkanoylamino, aroylamino, aryloxy;
aralkyl, optionally substituted by halo, loweralkyl, hydroxy, alkoxy, and amino groups wherein the alkyl groups contain from one to six carbon atoms;
$R_2$ is hydrogen or alkyl of from one to six carbon atoms optionally substituted by amino,
$R_3$ and $R_4$ may be connected together to form a proline moiety.

12. The composition of claim 11 wherein: $R_3$ and $R_4$ are joined through the nitrogen and carbon atoms to which they are respectively attached to form a five membered ring having the formula:

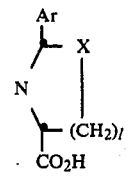

wherein X is $CH_2$, $CHOH$, $CHOCH_3$; 1 is one; and, Ar is phenyl, 2-hydroxyphenyl, or naphthyl.

13. The composition of claim 10 wherein:
R is the same or different and is hydrogen or loweralkyl;
$R_1$ is aralkyl optionally substituted by halo, loweralkyl, hydroxy, alkoxy, and amino groups wherein the alkyl groups contain one to four carbon atoms;
$R_2$ is hydrogen, alkyl of from one to six carbon atoms, or amino substituted alkyl of from one to six carbon atoms; and,
$R_3$ and $R_4$ are joined through the nitrogen and carbon atoms to which they are respectively attached to form a proline ring structure.

14. The composition of claim 13 wherein said compounds is:
N-(2-carboxy-4-phenylbutyl)-N-ethylaminocarbonyl-L-proline.

15. The composition of claim 13 wherein said compounds is:
N-(2-carboxy-4-phenylbutyl)-N-methylamino-carbonyl-L-proline.

16. The composition of claim 13 wherein said compound is:
N-[(2-ethoxycarbonyl)-4-phenylbutyl]-N-ethylamino-carbonyl-L-proline.

17. The composition of claim 13 wherein said compound is:
ethyl N-[(2-ethoxycarbonyl)-4-phenylbutyl]-N-ethylaminocarbonyl-L-prolinate.

18. The composition of claim 13 wherein said compound is:
N-(2-carboxy-4-phenylbutyl)-N-(4-aminobutyl)-aminocarbonyl-L-proline.

19. A method for treating hypertension which comprises administering to a patient in need of such treatment a pharmaceutically effective amount of a compound of the formula:

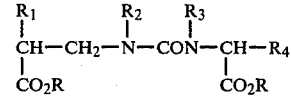

wherein:
R is same or different and is hydrogen, loweralkyl, aralkyl;
$R_1$ is alkyl of from one to ten carbon atoms which include branched, cyclic, and unsaturated alkenyl and alkynyl groups; substituted alkyl of from one to six carbon atoms and the substituent is amino, arylthio, aryloxy, hydroxy, arylamino, loweralkanoylamino, and aroylamino;
aralkyl optionally substituted by halo, loweralkyl, hydroxy, alkoxy, and amino groups wherein the alkyl groups contain from one to six carbon atoms;

$R_2$ is hydrogen, alkyl of from one to six carbon atoms optionally substituted by amino, loweralkylamino, arylamino, loweralkanoylamino, aroylamino, or aryl groups;

$R_3$ and $R_4$ may be connected together to form a proline moiety; and, a pharmaceutically acceptable salt thereof.

20. The method of claim 19 wherein:

R is the same or different and is hydrogen, loweralkyl, aralkyl;

$R_1$ is alkyl of from one to six carbon atoms optionally substituted by amino, hydroxyl, loweralkanoylamino, aroylamino, aryloxy, aralkyl, optionally substituted by halo, loweralkyl, hydroxy, alkoxy, and amino groups wherein the alkyl group contain from one to six carbon atoms;

$R_2$ is hydrogen or alkyl of from one to six carbon atoms optionally substituted by amino, or heteroaryl groups;

$R_3$ and $R_4$ may be connected together to form a proline moiety.

21. The method of claim 20 wherein: $R_3$ and $R_4$ are joined through the nitrogen and carbon atoms to which they are respectively attached to form five membered ring having the formula:

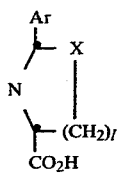

wherein X is $CH_2$, CHOH, $CHOCH_3$; 1 is one; and, Ar is phenyl, 2-hydroxyphenyl, or naphthyl.

22. The method of claim 19 wherein:

R is the same or different and is hydrogen or loweralkyl;

$R_1$ is aralkyl optionally substituted by halo, loweralkyl, hydroxy, alkoxy, and amino groups wherein the alkyl groups contain one to four carbon atoms;

$R_2$ is hydrogen, alkyl of from one to six carbon atoms, or amino substituted alkyl of from one to six carbon atoms; and, $R_3$ and $R_4$ are joined through the nitrogen and carbon atoms to which they are respectively attached to form a proline ring structure.

23. The method of claim 22 wherein said compound is:

N-(2-carboxy-4-phenylbutyl)-N-ethylaminocarbonyl-L-proline.

24. The method of claim 22 wherein said compound is:

N-(2-carboxy-4-phenylbutyl)-N-methylaminocarbonyl-L-proline.

25. The method of claim 22 wherein said compound is:

N-[(2-ethoxycarbonyl)-4-phenylbutyl]-N-ethylaminocarbonyl-L-proline.

26. The method of claim 22 wherein said compound is:

ethyl N-[(2-ethoxycarbonyl)-4-phenylbutyl]-N-ethylaminocarbonyl-L-prolinate.

27. The method of claim 22 wherein said compound is:

N-(2-carboxy-4-phenylbutyl)-N-(4-aminobutyl)aminocarbonyl-L-proline.

* * * * *